(12) United States Patent
Both et al.

(10) Patent No.: US 6,561,804 B2
(45) Date of Patent: May 13, 2003

(54) ONE-WAY RECEPTACLE FOR DENTAL FILLING MATERIAL

(75) Inventors: Adam Both, Hanau (DE); Ulrich Kläres, Alfter (DE); Ralf Luckau, Kahl (DE)

(73) Assignee: Degussa AG, Düsseldorf (DE)

( * ) Notice: Subject to any disclaimer, the term of this patent is extended or adjusted under 35 U.S.C. 154(b) by 48 days.

(21) Appl. No.: 09/827,321

(22) Filed: Apr. 6, 2001

(65) Prior Publication Data

US 2001/0047155 A1 Nov. 29, 2001

(30) Foreign Application Priority Data

Apr. 7, 2000 (DE) .......................................... 100 17 475

(51) Int. Cl.[7] ................................................. A61C 5/04
(52) U.S. Cl. ........................ 433/90; 206/63.5; 604/218
(58) Field of Search .............................. 433/90, 89, 80; 206/219, 63.5; 366/602; 604/218, 219

(56) References Cited

U.S. PATENT DOCUMENTS 4,472,141 A * 9/1984 Dragan ....................... 222/386
4,801,263 A * 1/1989 Clark ........................... 433/90
5,938,439 A * 8/1999 Mertins et al. ................ 433/90

FOREIGN PATENT DOCUMENTS

DE 90 14 769.3 2/1991
DE 196 51 981 7/1998

OTHER PUBLICATIONS

German language Search Report dated Mar. 15, 2001.

* cited by examiner

Primary Examiner—Kevin Shaver
Assistant Examiner—Melba Bumgarner
(74) Attorney, Agent, or Firm—Smith, Gambrell & Russell, LLP

(57) ABSTRACT

A receptacle for a filling material is disclosed, which is provided with a plunger which consists, at least in part, of a deformable material on a portion of the plunger which faces the nozzle. In one embodiment, the plunger disclosed can be a double plunger (a two-part plunger) displaceable axially into a defined end position in the direction of the nozzle, the deformable portion of which penetrates into the outlet channel of the nozzle, forcing out the dental filling material located there. It is preferred that the volume of deformable material of the nozzle penetrating into the nozzle is no greater than the volume of the nozzle through which the filling material passes.

5 Claims, 1 Drawing Sheet

ONE-WAY RECEPTACLE FOR DENTAL FILLING MATERIAL

BACKGROUND OF THE INVENTION

1. Field of the Invention

The invention relates to a one-way receptacle for dental filling material, which includes a cylindrical receptacle body having an outlet opening in the form of a nozzle, and an axially moveable plunger by means of which the dental filling material can be pressed out of the one-way receptacle through the nozzle.

2. Description of the Related Art

Dental medicinal products, e.g., quick-hardening filling materials, are charged into special one-way receptacles for use in dental practice. Such one-way receptacles usually contain an amount of filling material sufficient for a single use, which the dentist needs for the restoration of a prepared dental cavity. An instrument which can be used for multiple applications, a so-called applicator, is used for applying the filling material into the dental cavities. The one-way receptacle, however, which is mostly empty after the application but still has a small residue of filling material left in it, is not used again.

The known one-way receptacles of the type just discussed usually have a cylindrical receptacle body, one end of which is in the form of a bent, slightly conical nozzle. This nozzle is closed with a cap. The other end of the receptacle is closed by an axially moveable plunger. If the piston is pressed in the direction of the outlet opening designed as a nozzle with a suitable instrument, e.g., an applicator, the dental filling material is emptied through this nozzle. The shape of the plunger is adapted to the dimensions of the usable space in the one-way receptacle such that the dental filling material is completely pressed out of the receptacle when the plunger is at its end position.

The dental filling material which remains in the exit channel of the nozzle in the one-way receptacle cannot be used. The length of the nozzle and the diameter of the outlet channel are determined by the dental application and the viscosity of the dental filling material, so that the volume of the outlet channel cannot be arbitrarily reduced. Therefore, a relatively large residue of dental filling material generally remains unused in such one-way receptacles. Due to the usual high cost of dental products, this unusable filling material residue represents a substantial economic disadvantage in the use of these one-way receptacles.

An object of the invention, therefore, is to design a one-way receptacle so that the unusable residue of dental filling material remaining in the one-way receptacle after a dental application is reduced as much as possible. This object must be obtained without changing the design of the nozzle, because the shape of the nozzle is essentially predetermined by the viscosity of the filling material and the intended dental application.

SUMMARY OF THE INVENTION

These and other objects are achieved by the one-way receptacle according to the present invention, designed so that the unusable residue of dental filling material remaining in the one-way receptacle after a dental application is reduced as much as possible. This object is achieved without changing the design of the nozzle. The invention provides a plunger which consists, at least partially, of deformable material on the side facing the nozzle.

By displacement of the axially moveable plunger, the dental filling material is completely pressed out of the receptacle body. Further pressure on the plunger causes the deformable plunger material to penetrate at least partially into the nozzle, and pushes out the dental filling material there. An end position of the plunger is precisely determined, either by the external shape of the plunger part, consisting of non-deformable material, or is assured by attaining deformability of the plastic plunger part. The amount of dental filling material that additionally can be pressed out of the nozzle can also be determined through the volume of the deformable plunger material and the defined end position.

According to one embodiment of the invention, a plunger is provided which is a double plunger, which includes a nondeformable, hollow cylindrical plunger shell, open toward the nozzle, the shape of which is adapted to the dimensions of the usable space in the one-way receptacle. There is an opening on its rear side, as well as a radially symmetric plunger core of deformable material that is axially moveable, independently of it. During application, the plunger shell and the plunger core are first simultaneously displaced by pressure on the rear side of the plunger shell into the defined end position of the plunger shell, and the dental filling material is completely pressed out of the receptacle body. Through the opening on the rear side of the nondeformable plunger shell, additional pressure can then be exerted on the plunger core. The deformable material of the plunger core penetrates into the outlet channel of the nozzle and forces out the dental filling material there also. The extra construction expense for a plunger consisting of these several individual parts is low compared with the cost savings obtained by ensuring that all of the unusually expensive dental filling material is available for use.

The invention preferably provides that, in addition to the plunger core of deformable material, there is a nondeformable cylindrical ram in the cylindrical plunger shell facing the opening in the plunger shell. It is thus sufficient to exert pressure on the nondeformable ram through a comparatively small opening in the rear side of the plunger shell, which is uniformly transferred by it to the deformable plunger core. The external pressure required can be achieved by a concentric pressure sleeve acting on the rear side of the plunger shell, as well as by a pressing rod acting on the ram through the opening in the rear side of the plunger. The pressing rod and pressure sleeve expediently are components of an applicator adapted to such double plungers.

According to another embodiment of the invention, it is possible that the side of a two-part plunger facing the nozzle, and comprised of deformable material, is adapted in its original shaping to the receptacle body enclosing the usable space. Accordingly, the plunger consists of a nondeformable ram and a plunger tip of deformable material. If the plunger ram is displaced axially into the end position prescribed by its form inside the receptacle body, a portion of the deformable material of the plunger tip penetrates into the nozzle and forces out the dental filling material there. Because a one-way receptacle provided with such a deformable plunger does not differ externally from a commercial one-way receptacle provided with a one-part plunger, an applicator already available in dental practice can be used without modification.

According to a preferred embodiment, the invention provides that the volume of deformable material penetrating into the nozzle during displacement of the plunger corresponds, at best, to the volume of the outlet channel of the nozzle in its end position in the direction of the nozzle.

It is thus basically assured that under no circumstances does deformable plunger material emerge from the nozzle to become mixed into the prepared dental cavity during a dental application. This can be achieved for both plunger designs by an appropriate shaping of the nondeformable plunger parts.

BRIEF DESCRIPTION OF THE DRAWINGS

The invention will be better understood with reference to the accompanying drawings, in which.

DETAILED DESCRIPTION OF THE INVENTION

Figure 1:
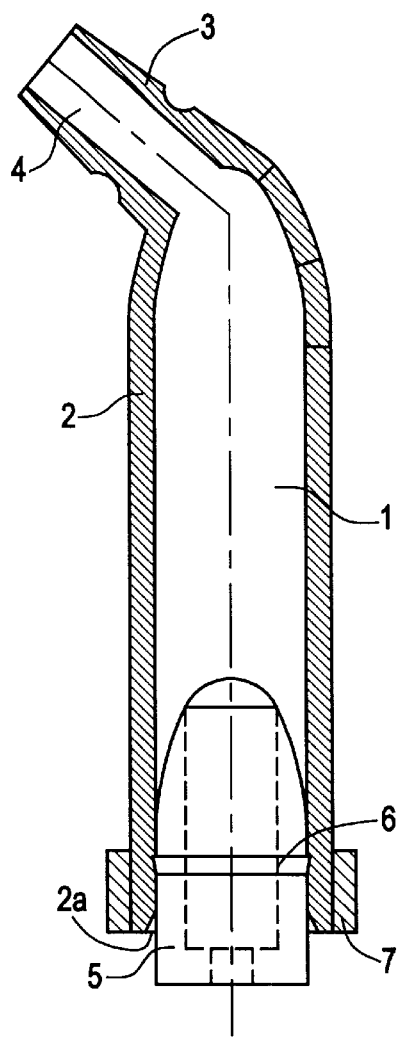
FIG. 1 shows a section through a oneway receptacle for dental filling material, consisting of a receptacle body with an outlet opening in the form of a nozzle and an axially moveable plunger.

The one-way receptacle of the embodiment shown in FIG. 1 has a cylindrical receptacle body 2 surrounding the usable space 1. At one end of the receptacle body 2 there is a nozzle 3 bent relative to the cylinder axis. The dental filling material located in the usable space 1 of the receptacle body 2 can be pressed out through an outlet channel 4. The pressure required for this is applied by a double plunger 5, axially moveable in the receptacle body 2. A radially projecting sealing lip 6 located on the double plunger 5 prevents the undesirable emergence of dental filling material at the plungerside opening 2a of the receptacle body 2. During filling, a necessary escape of air from usable space 1 of the receptacle body 2 can still occur, due to a venting profile of the sealing lip 6. A radially projecting edge 7 at the plunger end of the receptacle body 2 assures a better resistance to compression of the receptacles. This also simplifies production, in the positioning of the receptacle while being filled in a filling device, and the emptying with a suitable instrument, e.g., an applicator, during dental application.

Figure 2:
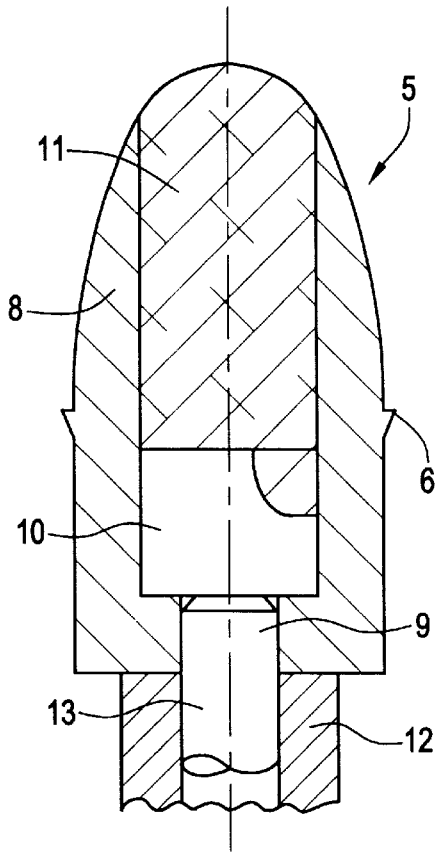
FIG. 2 shows a section through the plunger designed as a double plunger, consisting of a cylindrical plunger shell of nondeformable material and with an opening on the rear side, in which there are a nondeformable, rotationally symmetric ram and a rotationally symmetric plunger core of deformable material.

The embodiment example shown in FIG. 2 shows a double plunger 5 with a nondeformable cylindrical plunger shell 8 open to the nozzles, on the rear side of which there is an opening 9. A nondeformable ram 10 can be displaced through this opening 9 relative to the plunger shell 8, which effects a corresponding displacement of the plunger core 11 consisting of deformable material. During dental application, the entire double plunger 5 is first displaced axially by the receptacle body 2 into a definite end position by means of a concentric pressure sleeve 12. Then a pressure rod 13 displaces the ram 10 inside the plunger sleeve 8, thus pressing the plunger core 11, consisting of deformable material, partially into the outlet channel 4 of the nozzle 3 so that the dental filling material found therein is pressed out.

Figure 3:
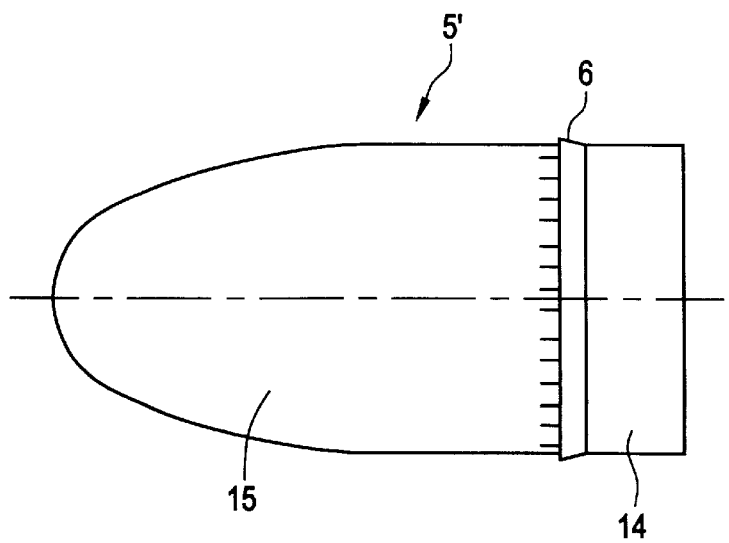
FIG. 3 shows a two-part plunger, consisting of a plunger ram of nondeformable material and a deformable plunger tip.

The embodiment example shown in FIG. 3 shows a two-part plunger 5', consisting of a nondeformable plunger ram 14 provided with a sealing lip 6, and a plunger tip 15, facing the nozzle 3, and which consists of deformable material. The original external form of the plunger tip 15 is adapted to the dimensions of the usable space 1 in the receptacle body 2.

Further variations and modifications will be apparent to those skilled in the art from the foregoing, and are intended to be encompassed by the invention according to the claims which follow.

German priority application 100 17 475.2 is relied on and incorporated herein by reference.

We claim:

1. A receptacle for a filling material, comprising:
   a cylindrical receptacle body which defines a usable space;
   an outlet opening, at an upper portion of the cylindrical receptacle body, provided with a nozzle which is in communication with the usable space; and a plunger comprised of a nondeformable plunger shell wherein the shell is, roughly cylindrical in form, adapted to the shape of the usable space, and open at a first and a second end thereof, and
   a radially symmetric plunger core comprised of a deformable material, which core is axially movable independently of the nondeformable plunger shell, by means of wherein the core the filling material is pressed out of the nozzle.

2. The receptacle for a filling material according to claim 1, further comprising a nondeformable cylindrical ram provided in the nondeformable plunger shell, by means of which nondeformable cylindrical ram the radially symmetric plunger core presses the filling material out of the nozzle.

3. The receptacle according to claim 1, wherein the deformable material of the plunger core which penetrates into the nozzle to press the filling material out of the nozzle has a volume, corresponding to nozzle volume through which the filling material is pressed.

4. The receptacle according to claim 1, wherein the deformable material of the plunger core which penetrates into the nozzle to press the filling material out of the nozzle has a volume no greater than the nozzle volume through which the filling material is pressed.

5. The receptacle according to claim 1, wherein the deformable material of the plunger core which penetrates into the nozzle to press the filling material out of the nozzle has a volume at least as large as the nozzle volume through which the filling material is pressed.

* * * * *